United States Patent
Stec, III et al.

(10) Patent No.: US 8,466,317 B1
(45) Date of Patent: Jun. 18, 2013

(54) PREPARATION OF INSENSITIVE BIS(2,2,-DINITROPROPYL) NITRAMINE (BDNPN)

(75) Inventors: Daniel Stec, III, Long Valley, NJ (US); Kathy Yang, Ledgewood, NJ (US); Gartung Cheng, Edison, NJ (US); Neha Mehta, Succasunna, NJ (US); Paritosh R. Dave, Bridgewater, NJ (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 89 days.

(21) Appl. No.: 13/176,996

(22) Filed: Jul. 6, 2011

(51) Int. Cl.
*C07C 243/02* (2006.01)
(52) U.S. Cl.
USPC .......................................... 564/110
(58) Field of Classification Search
USPC .......................................... 564/110
See application file for complete search history.

(56) References Cited

U.S. PATENT DOCUMENTS

| 2,901,512 | A | * | 8/1959 | Klager | 564/106 |
| 2,985,683 | A | * | 5/1961 | Klager | 564/106 |
| 3,000,949 | A | * | 9/1961 | Frankel et al. | 564/110 |

OTHER PUBLICATIONS

Technical Report ARAED-TR-96010, A. J. Bracuti, Molecular Structure of bis (2,2-dinitropropyI)-nitramine (BDNPN): Possible RDX Replacement, ARDEC, AED Energetics Warheads Division (AMSTA-AR-AEE-BR), Picatinny Arsenal, NJ 07806-5000 (Sep. 1996).*

* cited by examiner

*Primary Examiner* — Brian J Davis
(74) *Attorney, Agent, or Firm* — Henry S. Goldfine

(57) ABSTRACT

A method for preparing an insensitive bis(2,2-dinitropropyl) nitramine (BDNPN) as a fine powder which exhibits desirable insensitive munitions (IM) characteristics for use alone or compounded with other energetic materials such as RDX.

5 Claims, No Drawings

PREPARATION OF INSENSITIVE BIS(2,2,-DINITROPROPYL) NITRAMINE (BDNPN)

U.S. GOVERNMENT INTEREST

The inventions described herein may be manufactured, used and licensed by or for the U.S. Government for U.S. Government purposes.

FIELD OF THE DISCLOSURE

This disclosure relates generally to the field of energetic materials. More particularly, it pertains to an improved method for the preparation of insensitive bis(2,2-dinitropropyl)nitramine (BDNPN).

BACKGROUND OF THE DISCLOSURE

There is a continuing need for the development of insensitive energetic materials and in particular insensitive explosives and insensitive propellants. One such energetic material of particular interest is bis(2,2-dinitropropyl)nitramine.

SUMMARY OF THE DISCLOSURE

An advance in the art is made according to an aspect of the present disclosure directed to a method for preparing an insensitive bis(2,2-dinitropropyl)nitramine. Advantageously—and in sharp contrast to prior art methods for producing BDNPN which produces large crystals exhibiting an undesirable sensitivity—the method according to the present disclosure produces BDNPN as a very-fine, irregularly shaped material which surprisingly exhibits very desirable insensitive characteristics.

A method for preparing BDNPN according to an aspect of the present disclosure is substantially a simultaneous purification and particle-size modification process wherein crude BDNPN is dissolved in a water-soluble polar solvent and the resulting solution is then added to an ice/water slurry with stirring thereby producing the precipitation of pure BDNPN. Advantageously, the particle size of the pure BDNPN so produced is selectively variable, and is dependent upon the processing conditions (i.e., temperature, dilution, solvent, agitation rate) specifically employed to produce the physical properties and insensitivity desired.

DETAILED DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the disclosure.

By way of some additional background, it is noted that there exists a strong impetus to impart insensitive munitions (IM) characteristics to explosive and propellant formulations without compromising their performance. Of particular interest—and one aspect of the present disclosure—is the preparation and use of BDNPN to impart such insensitive characteristics to known energetic materials i.e., RDX—cyclotrimethylenetrinitramine—an explosive nitroamine widely used in military and industrial application which is also known as cyclonite, hexogen and T4.

Those skilled in the art will recognize that 3-Nitro-1,2,4-triazol-5-one (NTO) is an explosive component that is being explored as an potential insensitive replacement for RDX in explosive formulations. Although its performance is slightly less than that of RDX, NTO is thermally more stable and less sensitive to hazard stimuli. One infirmity associated with the use of NTO as an IM component is that its crystal morphology results in the isolation of acicular (needle-like) crystals that require further processing to obtain shape(s)/structure(s) suitable for use in IM formulations. As noted previously, an aspect of the present disclosure is the production of BDNPN having physical structure that advantageously formulates into a desirable IM energetic.

It is noted further that contemporary, prior art BDNPN production methods involves the dissolution of BDNPN crystals in a suitable solvent at elevated temperature and subsequently cooling the solution. This results in large crystalline BDNPN exhibiting impact sensitivity in the range of 25-35 cm. Grinding of these crystals to reduce particle size does not offer any enhanced insensitivity.

According to an aspect of the present disclosure, the process by which very fine particulate (non-needle) BDNPN exhibiting desirable IM characteristics is a simultaneous purification and particle size modification process. Advantageously, such a process interoperates with conventional processing equipment.

According to an aspect of the present disclosure, crude BDNPN is dissolved in a water-soluble polar solvent—preferably acetone at 25° C.-35° C. Those skilled in the art will appreciate that other This BDNPN solution is then added to an 1° C. to 4° C. ice/water slurry with continuous stirring. Pure (99%) BDNPN precipitates out of the solution. The precipitate is recovered and dried as very fine crystals/powder (non-needle shaped) and exhibits a particle size of approximately 5-25 microns. Advantageously this material can be utilized, without further processing, to prepare insensitive high explosive or propellant formulations.

Advantageously, the BDNPN so produced is surprisingly insensitive and exhibits an impact sensitivity over 100 cm and a shock sensitivity less than that of RDX.

At this point, while we have discussed and described the invention using some specific examples, those skilled in the art will recognize that our teachings are not so limited. Accordingly, the invention should be only limited by the scope of the claims attached hereto.

The invention claimed is:

1. A method of preparing insensitive bis(2,2-dinitropropyl) nitramine (BDNPN) suitable for use as an insensitive energetic comprising the steps of:

dissolving a quantity of BDNPN in a water-soluble polar solvent;

adding the BDNPN solution to an ice/water slurry with stirring such that BDNPN precipitates;

recovering the precipitated insensitive BDNPN;

wherein the recovered insensitive BDNPN has an impact insensitivity over 100 cm and a shock sensitivity less than that of RDX.

2. The method of claim 1 wherein the water-soluble polar solvent is acetone.

3. The method of claim 1 wherein the acetone is at a temperature of 25° C. to 35° C.

4. The method of claim 1 wherein the ice/water slurry is at a temperature of 1° C. to 4° C.

5. The method of claim 1 wherein the insensitive BDNPN exhibits a particle size of 5-25 microns.

* * * * *